United States Patent
Sauer

(10) Patent No.: US 10,682,158 B2
(45) Date of Patent: Jun. 16, 2020

(54) CANNULATION DEVICE AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 606 days.

(21) Appl. No.: 15/411,281

(22) Filed: Jan. 20, 2017

(65) Prior Publication Data

US 2017/0209673 A1   Jul. 27, 2017

Related U.S. Application Data

(60) Provisional application No. 62/281,768, filed on Jan. 22, 2016.

(51) Int. Cl.
| | |
|---|---|
| *A61B 17/34* | (2006.01) |
| *A61B 17/3209* | (2006.01) |
| *A61B 17/00* | (2006.01) |

(52) U.S. Cl.
CPC ...... *A61B 17/3423* (2013.01); *A61B 17/3209* (2013.01); *A61B 17/3415* (2013.01);
(Continued)

(58) Field of Classification Search
CPC .......... A61B 17/07207; A61B 17/0469; A61B 18/1445; A61B 17/3496; A61B 17/29; A61B 17/068; A61B 17/1285; A61B 17/320016; A61B 17/00234; A61B 10/0275; A61B 17/0218
(Continued)

(56) References Cited

U.S. PATENT DOCUMENTS

| | | | |
|---|---|---|---|
| 3,714,945 A | | 2/1973 | Stanley |
| 5,441,041 A | * | 8/1995 | Sauer ..................... A61B 17/34 600/106 |

(Continued)

FOREIGN PATENT DOCUMENTS

EP   2891502   1/2008

OTHER PUBLICATIONS

Jan. 1, 2009; Product Literature; Port Access EndoDirect System Quick Reference Guide.
(Continued)

*Primary Examiner* — Manuel A Mendez
(74) *Attorney, Agent, or Firm* — David J. Gervasi; Christopher B. Miller

(57) ABSTRACT

A cannulation device is disclosed, having a fixed blade, a retractable wedge, and an adjustment nut for mating with a cannula or a cannula assembly. Another cannulation device is disclosed, having a tube with proximal and distal ends. The fixed blade, coupled to the distal end of the tube, comprises a transition edge configured to cover a lead edge of a cannula. The cannulation device has a control rod movable within the tube; a retractable wedge; an actuator coupled to the control rod; and is configured to move the retractable wedge from a piercing position, where the retractable wedge is aligned with the fixed blade, to a retracted position where the retractable wedge has been retracted within the tube. The cannulation device has a cannula adapter and an adjustment nut movable to change a distance between the adjustment nut and the fixed blade.

16 Claims, 15 Drawing Sheets

(52) U.S. Cl.
CPC ...... *A61B 17/3421* (2013.01); *A61B 17/3496* (2013.01); *A61B 2017/00252* (2013.01); *A61B 2017/3425* (2013.01)

(58) Field of Classification Search
USPC ........................................................ 606/185
See application file for complete search history.

(56) References Cited

U.S. PATENT DOCUMENTS

| | | | | |
|---|---|---|---|---|
| 5,611,352 | A | * | 3/1997 | Kobren .............. A61B 10/0275 600/564 |
| 5,620,456 | A | * | 4/1997 | Sauer ................ A61B 17/3417 604/164.01 |
| 2006/0200182 | A1 | * | 9/2006 | Prosek .................. A61B 17/34 606/185 |

OTHER PUBLICATIONS

Jan. 1, 2008; Product Literature; Port Access Quick Reference Guide.

\* cited by examiner

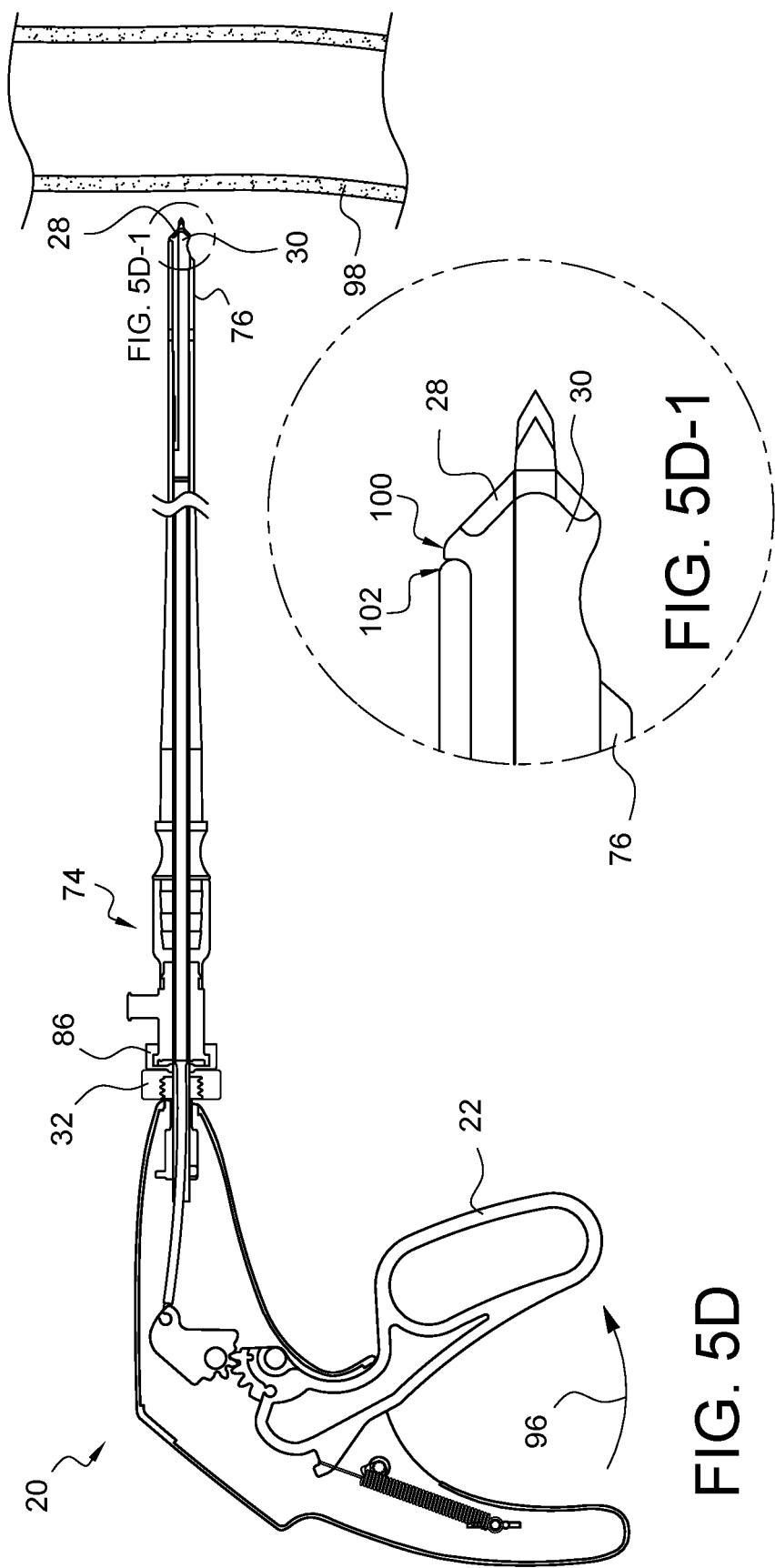

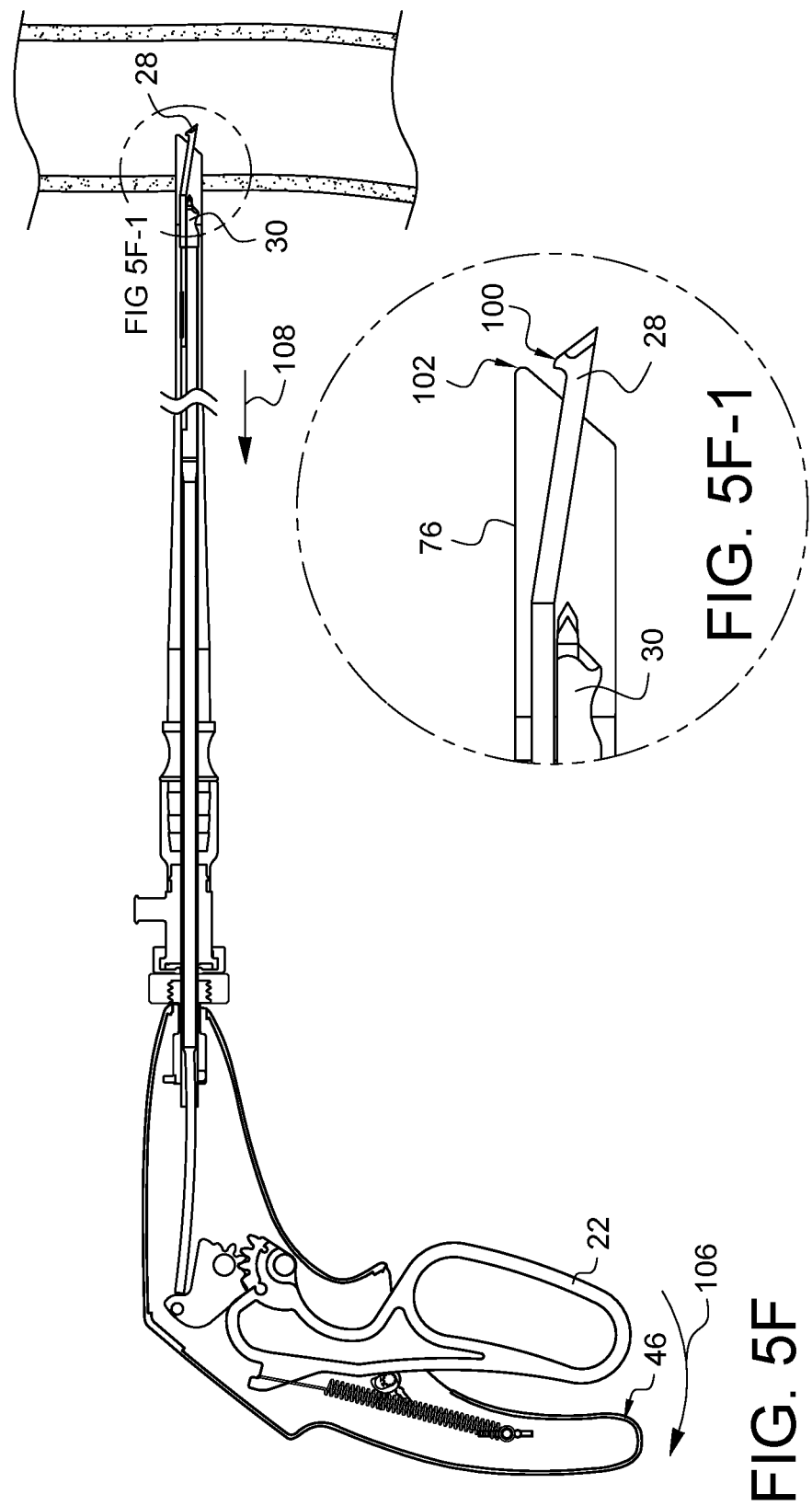

CANNULATION DEVICE AND METHODS THEREOF

RELATED APPLICATION

This patent application claims priority to U.S. Provisional Patent Application No. 62/281,768 filed Jan. 22, 2016 and entitled "CANNULATION DEVICE AND METHODS THEREOF". The 62/281,768 application is hereby incorporated by reference in its entirety.

FIELD

The claimed invention relates to surgical cannulation, and more specifically a cannulation device and methods thereof.

BACKGROUND

Various types of surgery require a surgeon to place a cannula within a vessel, such as the aorta, in order to gain fluid access to the vessel. For example, in many cardiac surgeries, blood returning to the heart may be diverted to one or more cannulas for removal from the patient's body in order to pass the blood through a cardio pulmonary bypass (CPB) machine that reoxygenates the blood before returning the blood to the aorta on the output side of the heart. It is desirable to minimize the amount of time it takes to establish cannulation so that CPB may be established without undue delay and so that surgery times may be reduced in order to improve patient outcomes and reduce surgical team fatigue. Unfortunately, at odds with this desire is the reality that more and more surgeries are being done with minimally invasive techniques to reduce patient trauma and speed recovery times. The small access sites afforded surgeons with minimally invasive techniques may either make cannulation difficult (time consuming) or may prevent surgeons from using the minimally invasive techniques in the first place. Therefore, it would be desirable to have a cannulation device and methods which would enable surgeons to place a cannula efficiently in a vessel while operating through a minimally invasive surgical access site.

SUMMARY

A cannulation device is disclosed. The cannulation device has a fixed blade, a retractable wedge, and an adjustment nut for mating with a cannula or a cannula assembly.

Another cannulation device is disclosed. The cannulation device has a tube having a proximal end and a distal end. The cannulation device also has a fixed blade coupled to the distal end of the tube. The fixed blade comprises a transition edge configured to cover a lead edge of a cannula. The cannulation device further has a control rod movable within the tube and a retractable wedge coupled to the control rod. The cannulation device also has an actuator coupled to the control rod and configured to move the retractable wedge from a piercing position where the retractable wedge is aligned with the fixed blade to a retracted position where the retractable wedge has been retracted within the tube. The cannulation device further has an adjustment nut movable to change a distance between the adjustment nut and the fixed blade. The cannulation device also has a cannula adapter.

A method of cannulation is disclosed. While retracting a retractable wedge, a fixed blade is pushed past a distal end of a cannula, such that a transition edge of the fixed blade clears a leading edge on the distal end of the cannula. After the fixed blade clears the leading edge of the cannula, the retractable wedge is extended out of the distal end of the cannula to a piercing position in alignment with the fixed blade which provides cover for the leading edge of the cannula. Then the fixed blade and retractable wedge are used to pierce a vessel so that the lead edge of the cannula follows into the vessel.

BRIEF DESCRIPTION OF THE DRAWINGS

FIGS. 5A-5G schematically illustrate a surgical situation and example of using the cannulation device with the cannula assembly in order to place the cannula into a vessel.

DETAILED DESCRIPTION

Figure 1:
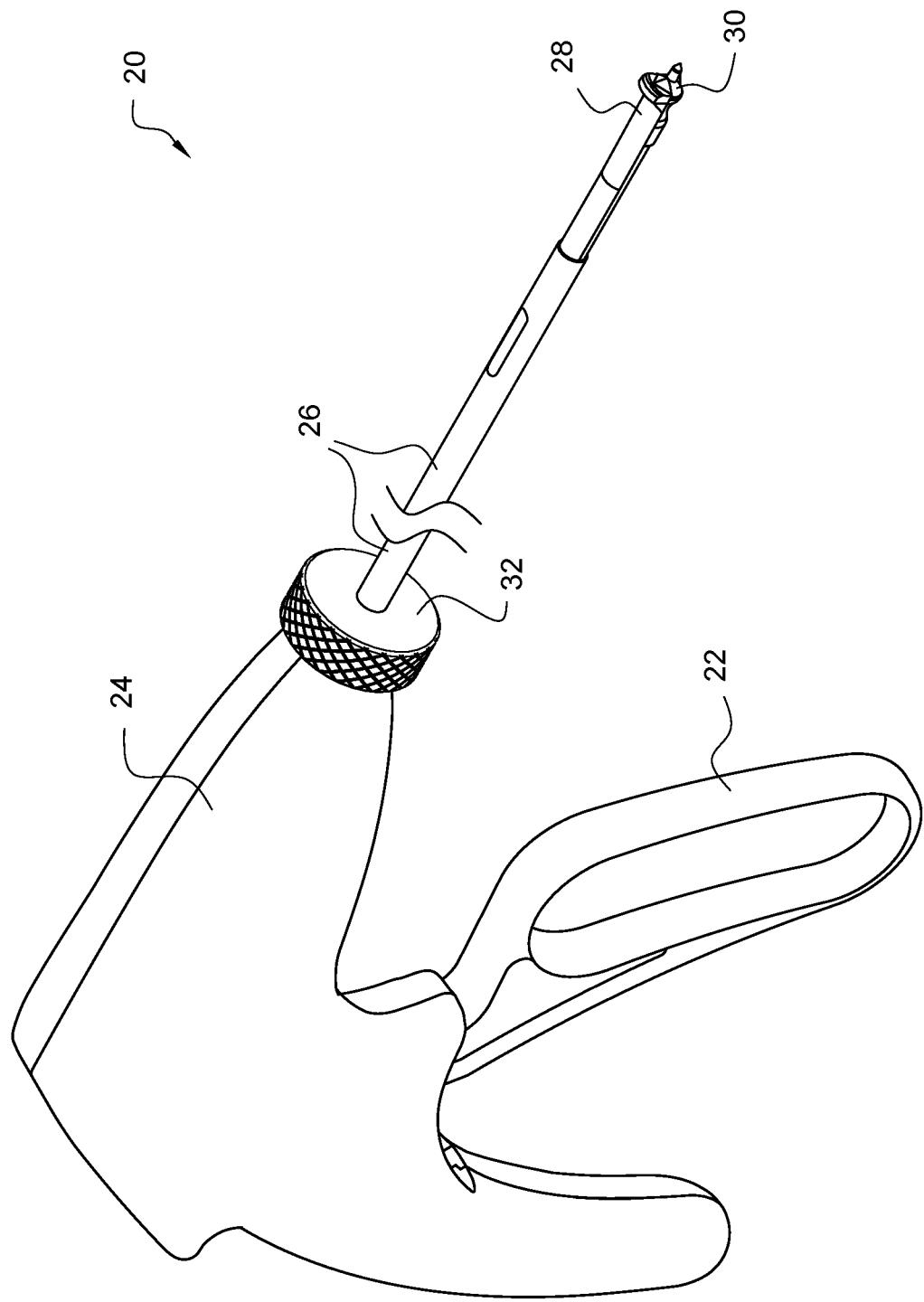
FIG. 1 is a perspective view of one embodiment of a cannulation device.

FIG. 1 is a perspective view of one embodiment of a cannulation device 20. The cannulation device 20 has an actuator handle 22 that is pivotably coupled to a housing 24. A tube 26 is coupled to the housing 24, and a fixed blade 28 is coupled to the tube 26. Under the fixed blade 28, a retractable wedge 30 is axially moveable from the fully extended position shown in FIG. 1 to a retracted position which will be illustrated later in this discussion. An adjustment nut 32 is positioned around the tube 26.

Figure 2:
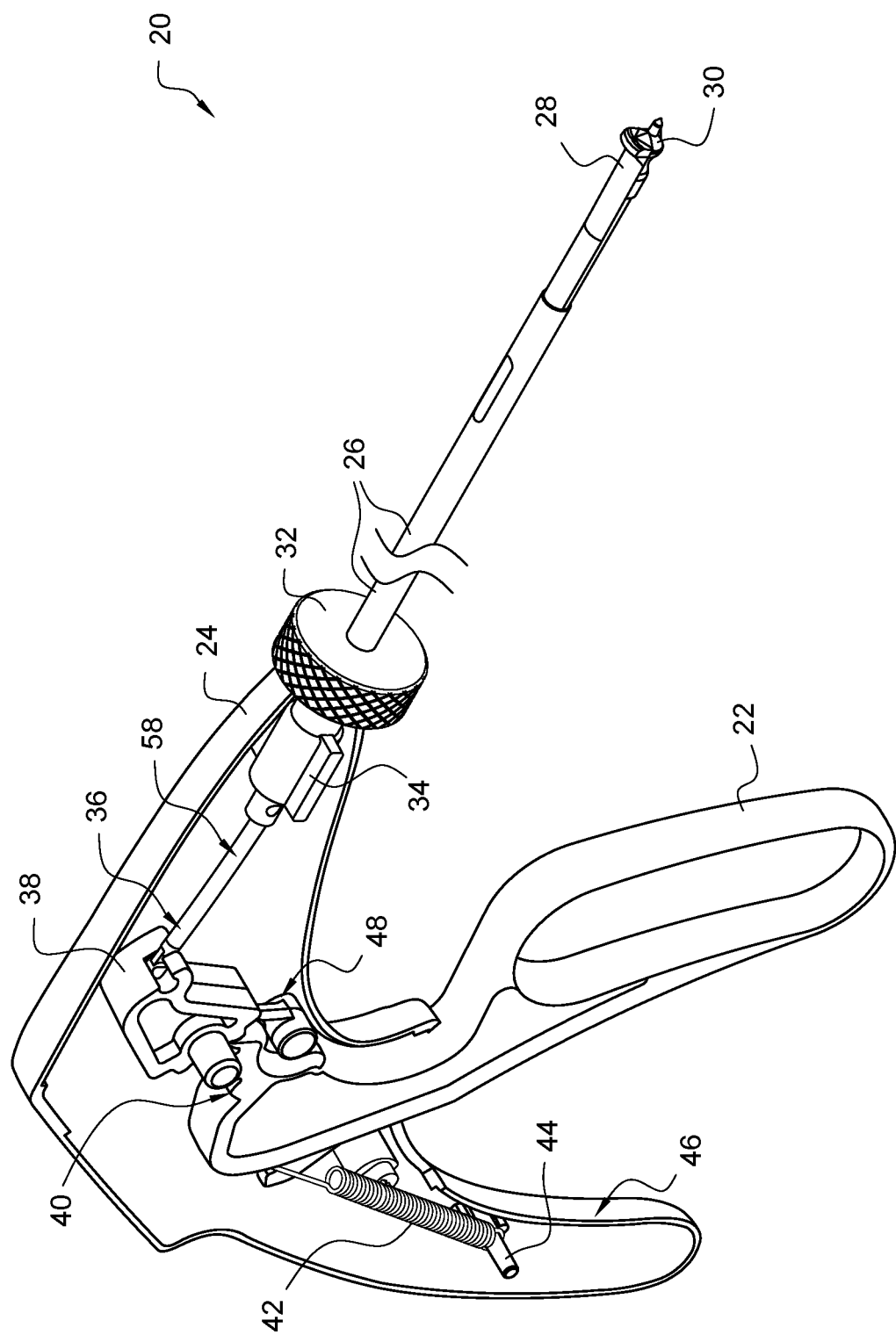
FIG. 2 is a partially exposed perspective view of the cannulation device of FIG. 1.

FIG. 2 is a partially exposed perspective view of the cannulation device 20 of FIG. 1. A portion of the housing 24 has been removed from FIG. 2 in order to show the components of the device which were covered therein in this embodiment. The tube 26, which passes through the adjustment nut 32, is coupled to an adapter 34 which is held by the housing 24. The adapter 34 has a channel therein (not visible in this view) through which a proximal end 36 of a control rod 58 has been passed. The control rod 58 is coupled to or may be formed continuously with the retractable wedge 30. In this embodiment, the control rod 58 is coupled to a reverse gear 38. The reverse gear 38 is moveable by a corresponding lever gear 40 which is part of the actuator handle 22. A spring 42 coupled between a fixed spring anchor 44 and the actuator handle 22 such that the handle 22 is biased away from a grip 46 formed by the housing 24. With the handle 22 in the position shown in FIGS. 1 and 2, the retractable wedge 30 is not retracted, but is, instead, in a piercing position.

Figure 3:
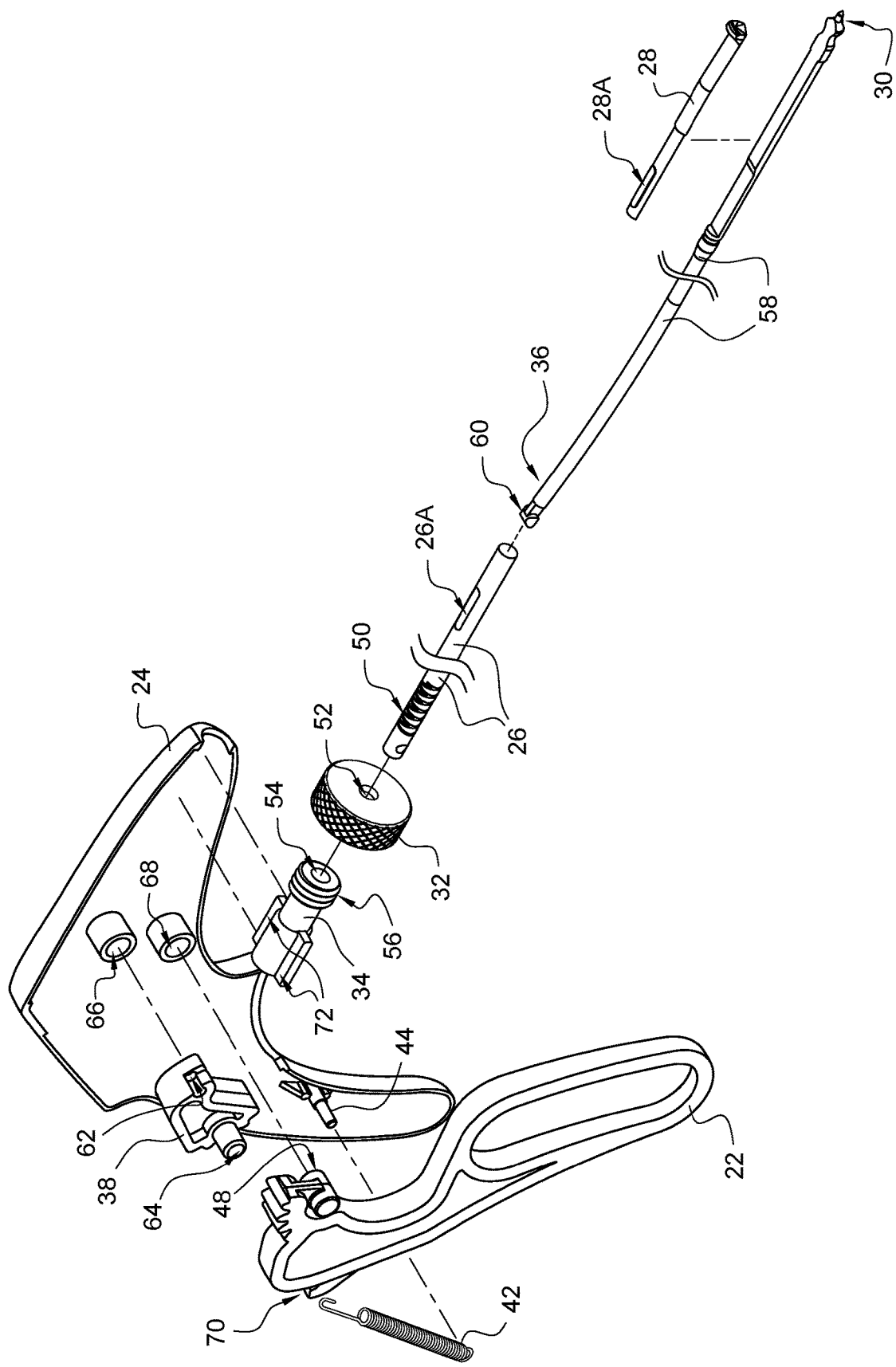
FIG. 3 is an exploded perspective view of the cannulation device of FIG. 2.

FIG. 3 is an exploded perspective view of the cannulation device 20 of FIG. 2. The proximal end 50 of the tube 26 is passed through a hole 52 in the adjustment nut 32 and coupled inside a tube receiver end 54 of the adapter 34. Threads inside the adjustment nut 32 (threads not visible in this view) correspond to adapter threads 56 on the adapter 34, and the adjustment nut 32 may be threaded onto the adapter 34. In this embodiment, the retractable wedge 30 is formed continuously with the control rod 58 as part of the same part. In other embodiments, these portions could be separate parts and would need to be coupled. The fixed blade 28 is placed against the distal end of the retractable wedge tip 30, while the proximal end 36 of the control rod 58 is inserted into the tube 26, and passed out through the adapter 34. In this embodiment, a key 28A on the fixed blade 28 engages a key receiver 26A in the tube 26 in order to prevent the fixed blade from sliding relative to the tube 26. A keyed portion 60 on the proximal end 36 of the control rod 58 is coupled to a control rod interface 62 on the reverse gear 38 after passing through the adapter 34. Reverse gear axles 64 are mated with corresponding reverse gear axle bosses 66 on the housing 24. Given the exposed perspective of FIG. 3, it should be noted that the visible reverse gear axle 64 mates with a boss in the housing that has been removed to expose the working parts (and therefore is not visible). Similarly, the visible reverse gear axle boss 66 mates with a gear axle 64 which is not visible from this perspective.

With the retractable wedge 30 fully extended in a piercing position, the actuator handle 22 can be pivotably coupled to the housing 24 while the handle 22 is fully extended. In doing this, axles 48 of the handle 22 are placed within corresponding lever axle bosses 68 of the housing 24. The spring 42 is coupled between a spring attachment point 70 on the handle 22 and a fixed spring anchor 44 on the housing 24.

The adapter 34 has housing interface wings 72 which mate with corresponding features (not shown, but known to those skilled in the art) on the inside of the housing 24. Although only one half of the housing 24 is shown in this exposed exploded view, it should be understood that a corresponding half of the housing (not shown) would couple with the visible housing 24 half to hold the adapter 34 in place while providing for pivotable movement of the actuator handle 22 and reverse gear 38 so that the retractable wedge 30 may be moved as described further below.

Figure 4A:
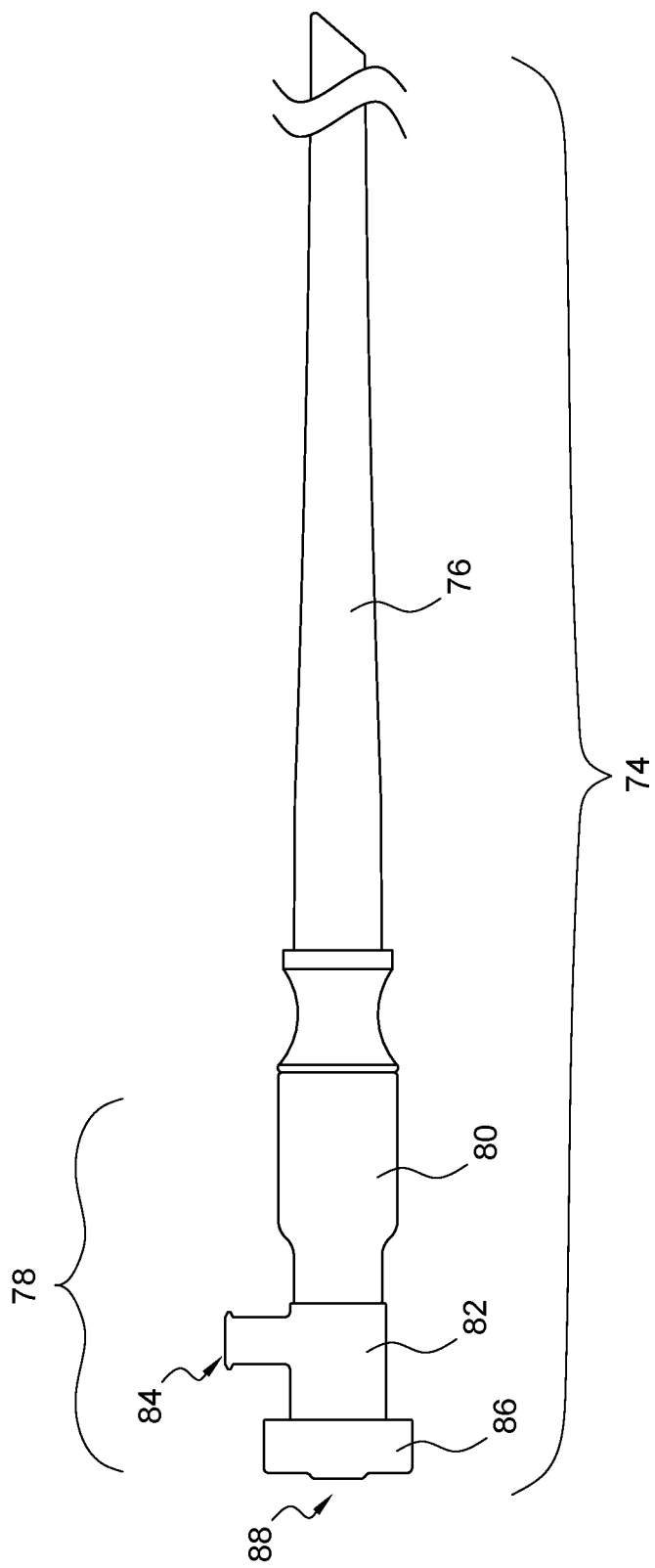
FIG. 4A is an embodiment of a cannula assembly.
Figure 4B:
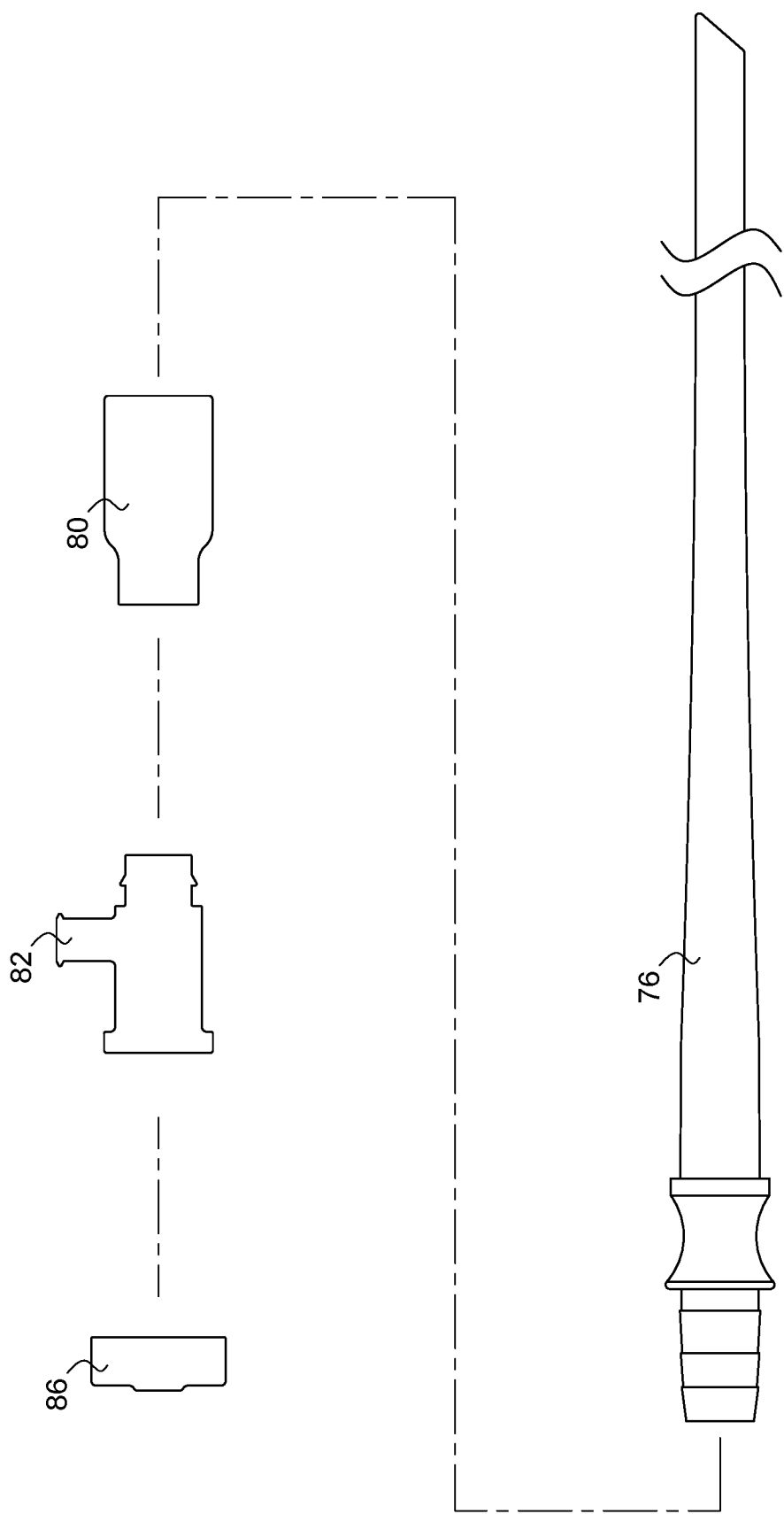
FIG. 4B is an exploded side view of the cannula assembly of FIG. 4A.
Figure 4C:
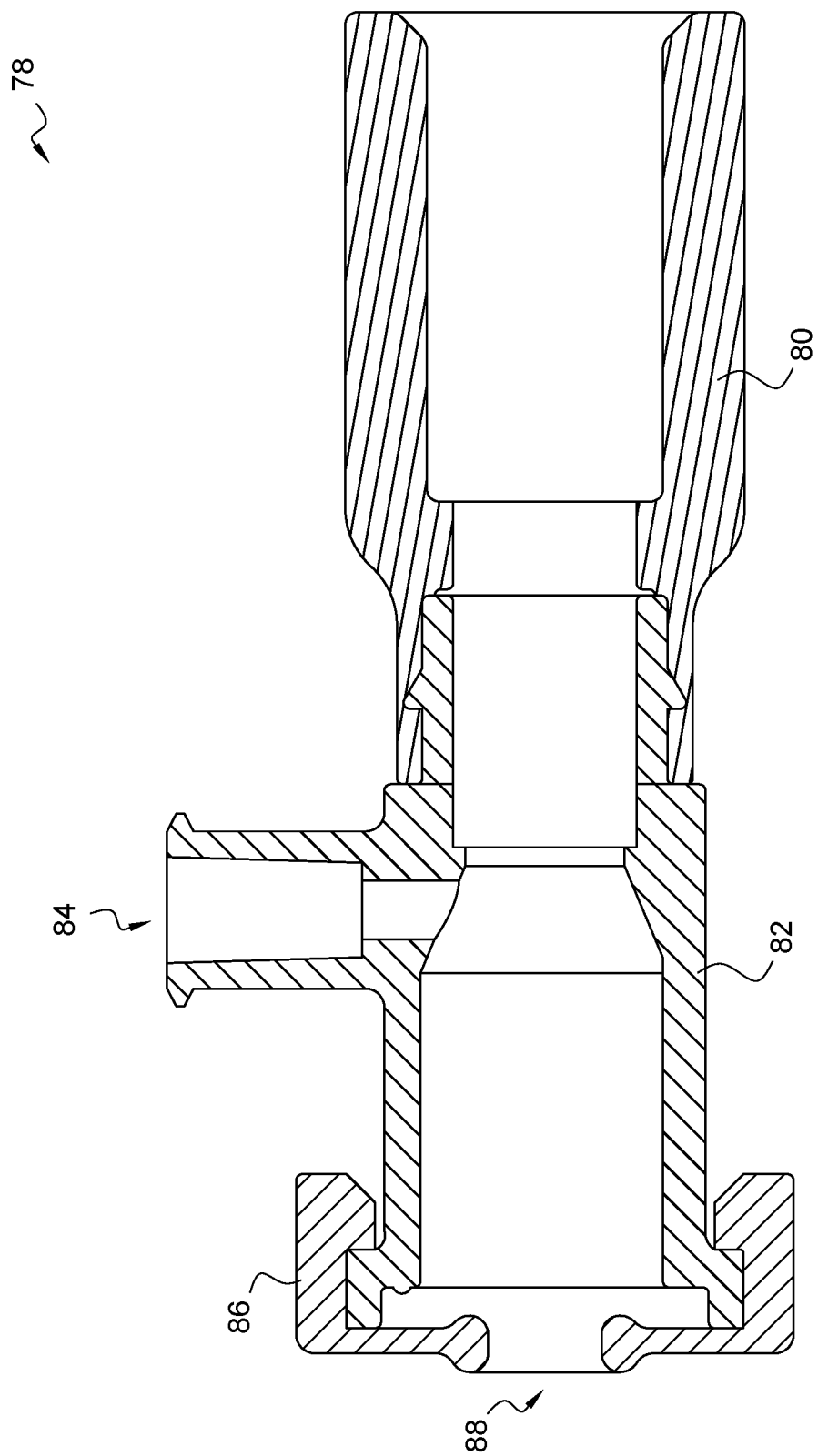
FIG. 4C is a side cross-sectional view of a cannula adapter.

The cannulation device 20 is intended to interact with a cannula assembly 74, such as the one schematically illustrated in the side view of FIG. 4A. In the embodiment of FIG. 4A, the cannula assembly 74 has a cannula 76 and a cannula adapter 78. Different embodiments and sizes of the cannulation device, discussed previously, may be configured to work with a variety of types of cannulas 76. As just one non-limiting example, the cannula 76 used herein is a Medtronic 71422 Femoral Venous Cannula. In this embodiment, the cannula adapter 78 includes a strain relief 80, a hub body 82, and a sealing cap 86. The hub body 82 may include a fluid port 84 which may be selectively capped or coupled to tubing in order to provide fluid access. The sealing cap 86 has a device receiver 88 which is sized to accommodate the tube 26 of the cannulation device (not shown in this view). FIG. 4B is an exploded side view of the cannula assembly 74. FIG. 4C is a side cross-sectional view of the cannula adapter 78.

Figure 5A:
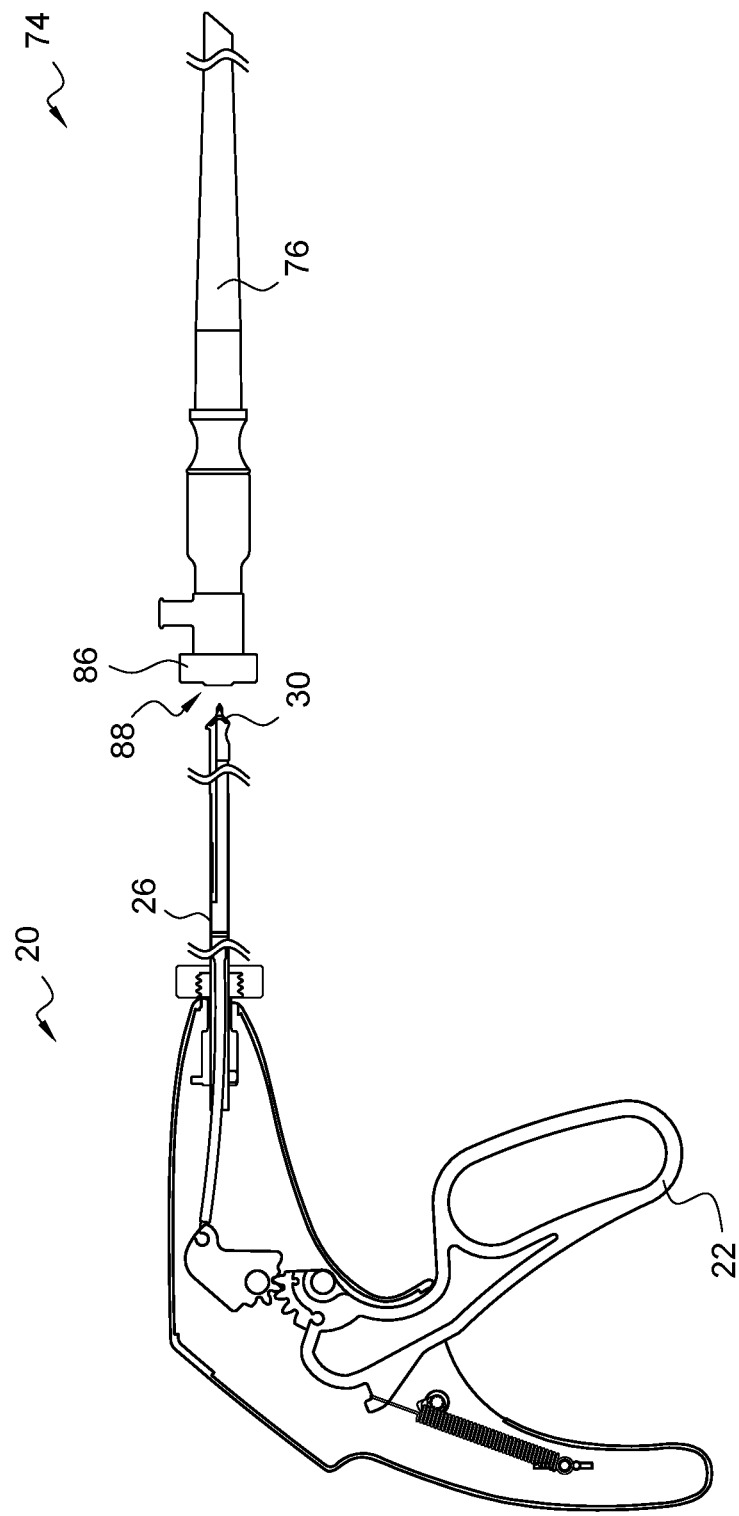
Figure 5B:
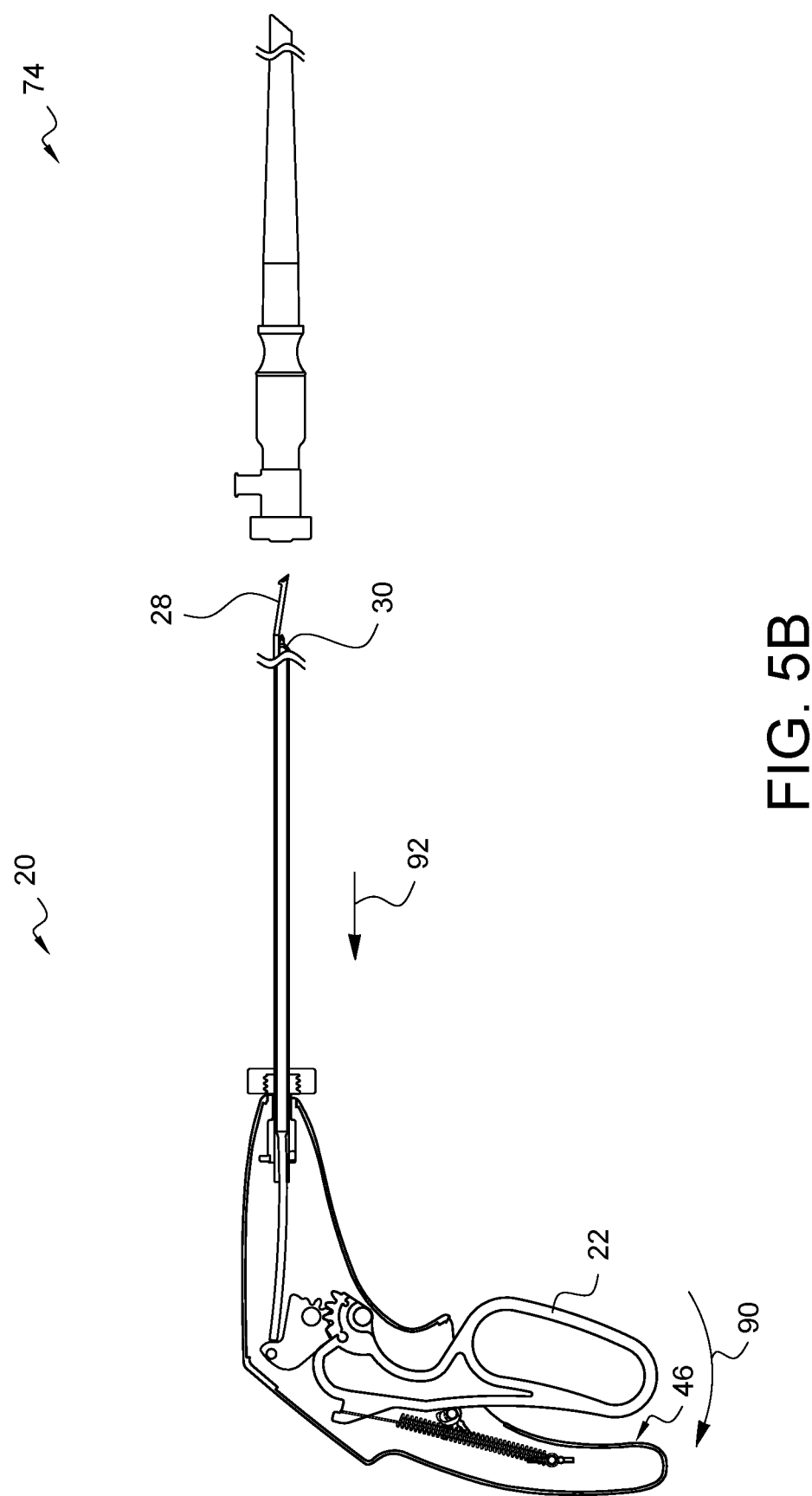
Figure 5C:
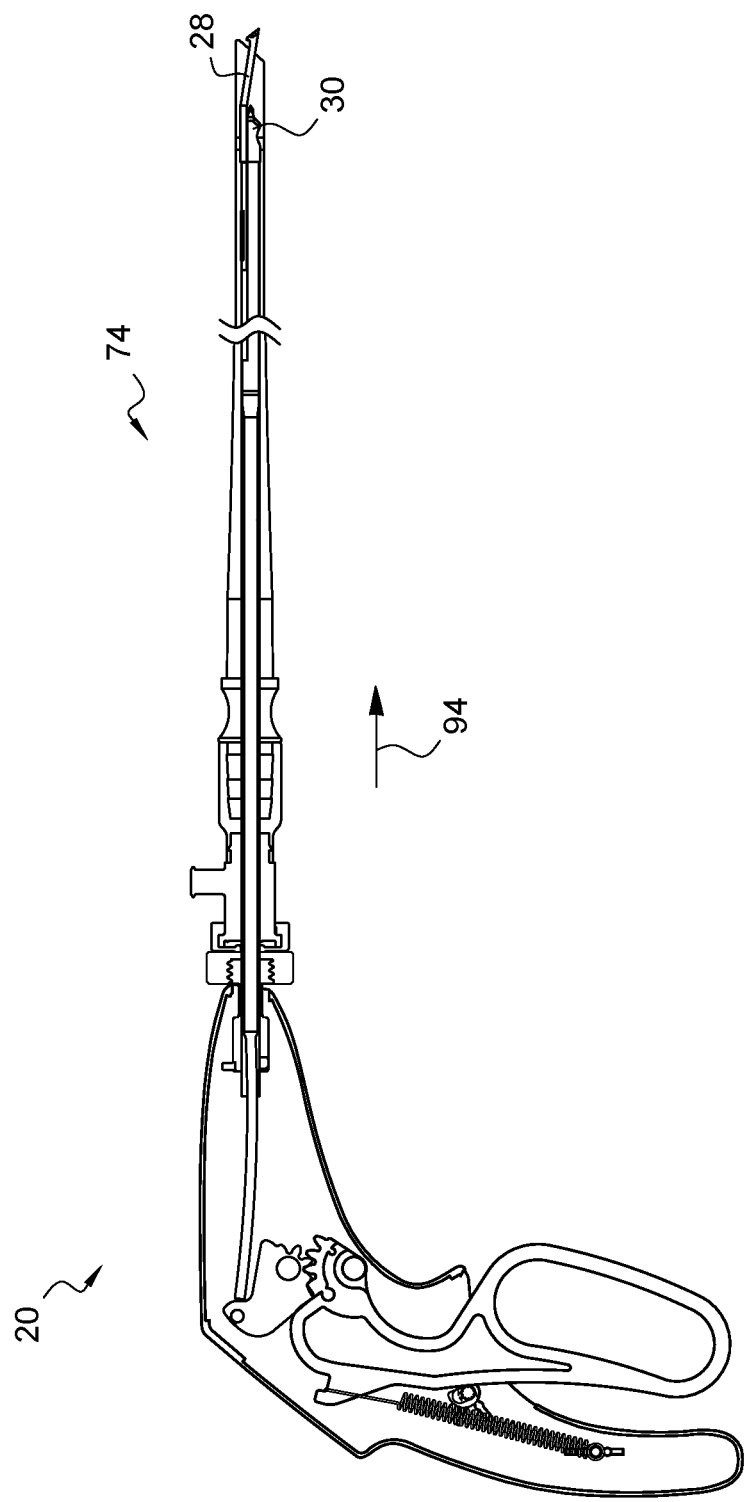

FIGS. 5A-5G schematically illustrate a surgical situation and example of using the cannulation device 20 with the cannula assembly 74 in order to place the cannula 76 into a vessel. Portions of the cannulation device 20 and cannula assembly 74 are shown in quasi cross-sectional or transparent views so that hidden movements and covered parts can be seen. In FIG. 5A, the actuator handle 22 is in its resting position, and the retractable wedge 30 is in a corresponding piercing position. The tube 26 of the cannulation device 20 is aligned with the device receiver 88 of the sealing cap 86 on the cannula assembly 74. As illustrated in FIG. 5B, the handle 22 is moved 90 towards the grip 46, causing the retractable wedge 30 to move proximally 92. The proximal movement 92 of the retractable wedge 30 enables the fixed blade 28 to fall down, reducing the effective area presented by the combined fixed blade 28 and retractable wedge 30. As shown in FIG. 5C, the cannulation device 20 can be inserted 94 into the cannula assembly 74 while the retractable wedge 30 is retracted. As shown in FIG. 5D, the handle 22 can be released 96, causing the wedge 30 to move distally out the end of the cannula 76, pushing the fixed blade 28 back to its original alignment. A vessel 98 is schematically illustrated in side cross-sectional view, waiting to be cannulated.

The interface between the sealing cap 86 and the adjustment nut 32 controls how far the fixed blade 28 and wedge 30 will extend out the end of the cannula 76. FIG. 5D-1 is an enlarged view of the end of the cannula 76, showing the fixed blade 28 and wedge 30 relative to the cannula 76. The adjustment nut 32 can be rotated to ensure a smooth transition between a transition edge 100 of the fixed blade 28 and a cannula leading edge 102. The cannula leading edge 102 is not typically strong enough or sharp enough to pierce a tissue on its own, but the transition edge 100 of the fixed blade 28 is positioned to assist with any piercing while making it easy to insert the cannula 76 into an opening created by the blade 28 and wedge 30 as will be illustrated below.

Typically, surgeons will place one or more pursestring sutures around an intended cannulation site before placing the cannula. The one or more pursestring sutures are then in-place to be tightened around the cannula after it is inserted into the vessel to help maintain a tight seal of the tissue around the cannula. Since pursestring sutures are known in the art, we are not including their placement in FIGS. 5A-5G for simplicity.

Figure 5E:
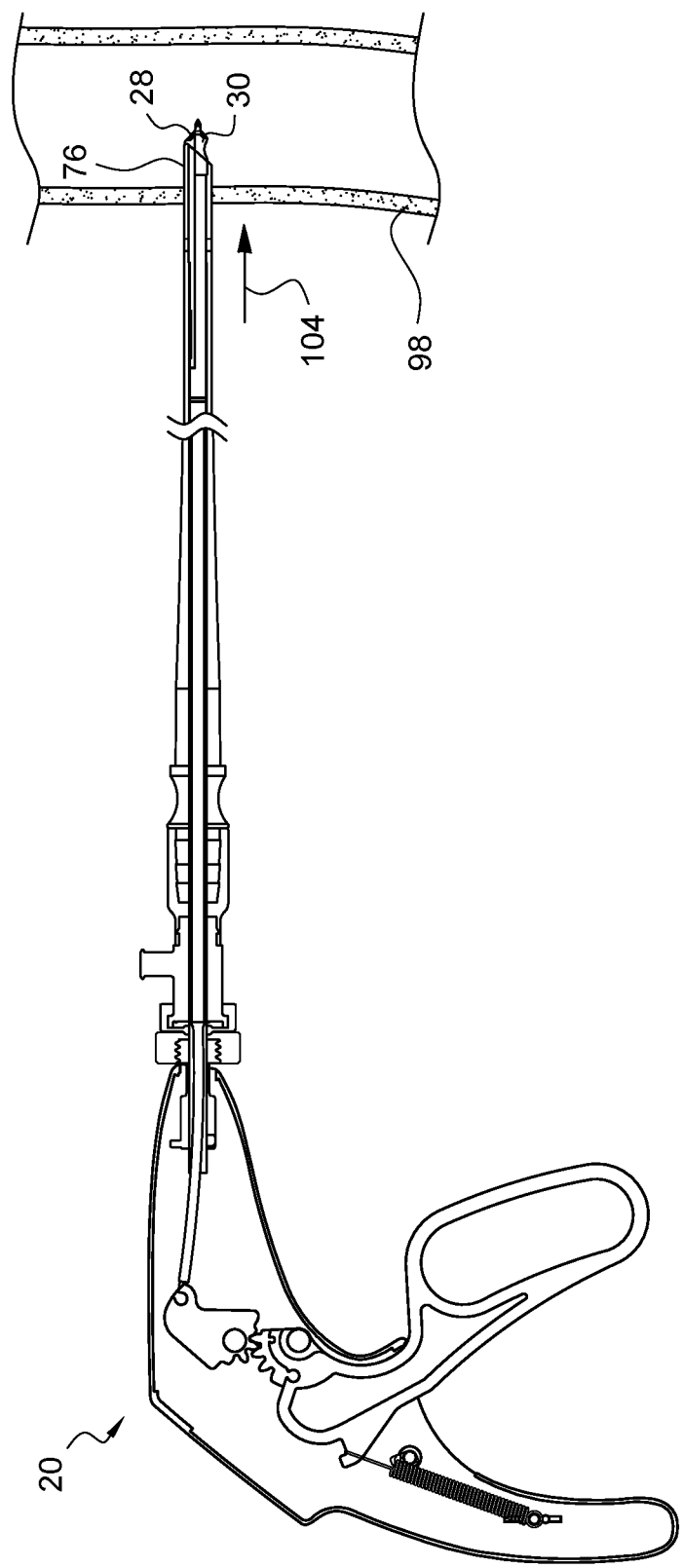
Figure 5G:
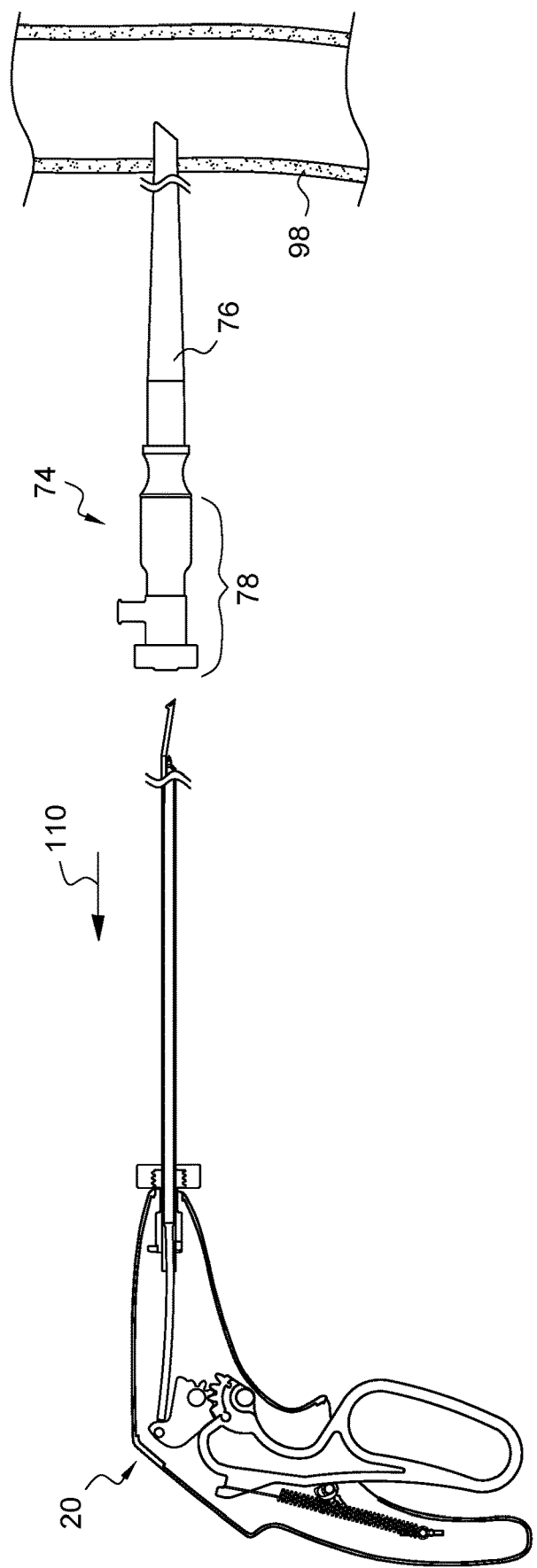

As illustrated in FIG. 5E, the cannulation device 20 can be pushed 104 against the vessel 98. The blade 28 and wedge 30 work together to create an incision in the vessel 98, allowing the cannula 76 to be advanced into the vessel 98. As illustrated in FIG. 5F, the handle 22 can be squeezed 106 back towards the grip 46, creating a proximal motion 108 of the retractable wedge 30 which also allows the transition edge 100 of the fixed blade 28 to fall clear of the cannula leading edge 102. This can be seen more clearly in the enlarged view of FIG. 5F-1. As illustrated in FIG. 5G, the cannulation device 20 can then be withdrawn 110 from the cannula assembly 74 which is left behind in the vessel 98. The cannula adapter 78 may be removed from the cannula assembly 74, while the cannula 76 is left in-place to be capped or connected to tubing, such as a line to/from a cardio-pulmonary bypass (CPB) machine. Alternately, the cannula assembly 74 may be capped or connected to such tubing, as desired.

Figure 6:
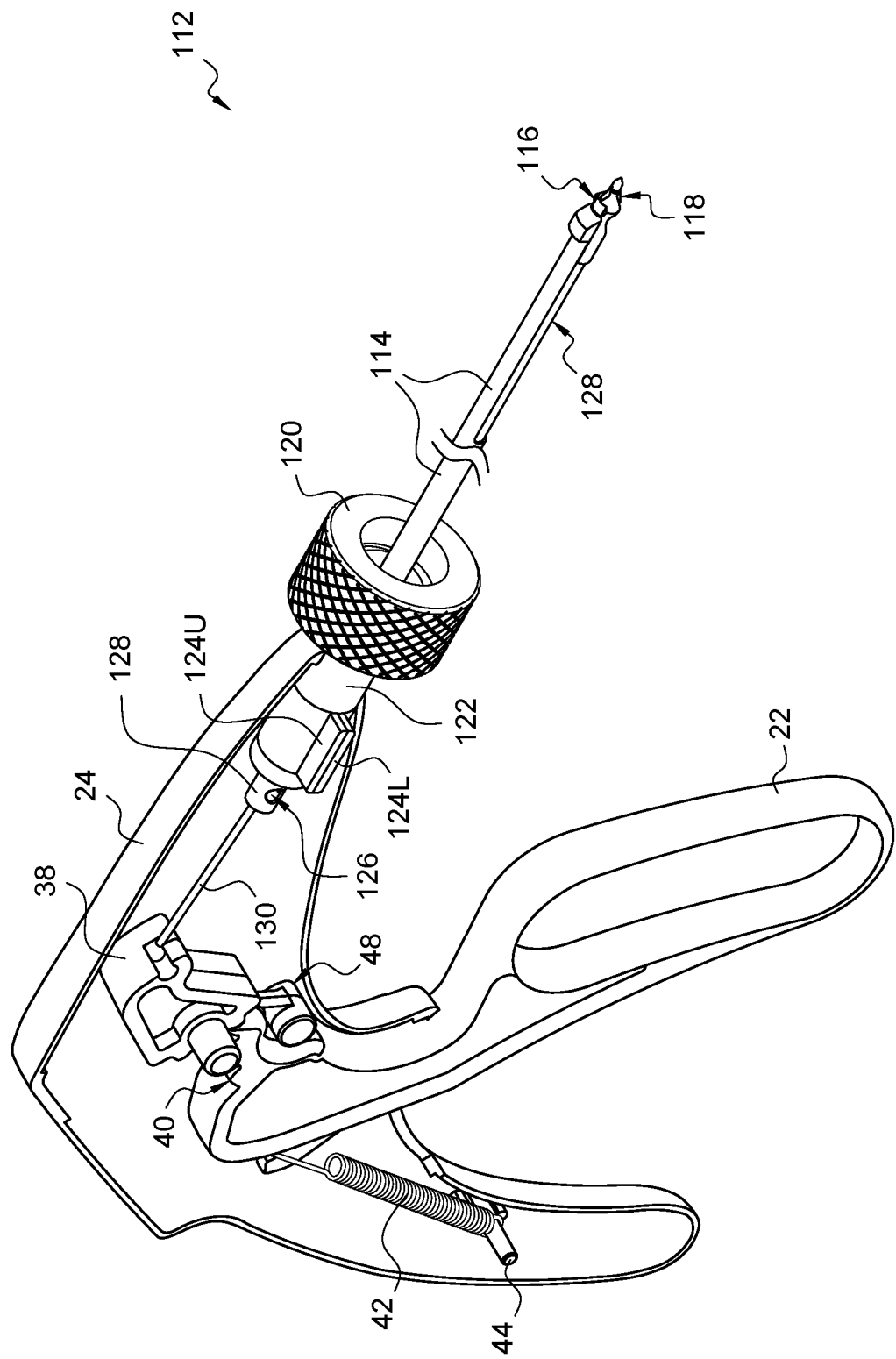
FIG. 6 illustrates another embodiment of a cannulation device in a partially exposed perspective view.

FIG. 6 illustrates another embodiment of a cannulation device 112 in a partially exposed perspective view. The cannulation device 112 has an actuator handle 22 that is pivotably coupled to a housing 24. A tube 114 is coupled to the housing 24, and in this embodiment, the fixed blade 116 is a continuous extension of the tube 114. Under the fixed blade 116, a retractable wedge 118 is axially moveable from the fully extended position shown in FIG. 6 to a retracted position similar to the one discussed previously. An adjustment nut 120 is positioned around the tube 114. The tube 114, which passes through the adjustment nut 120, is coupled to an adapter 122 which is held in this embodiment by upper and lower clamshell brackets 124U, 124L which are in turn held by the housing 24. The adapter 122 has a channel therein (not visible in this view) through which a proximal end 126 of a control rod 128 has been passed. The control rod 128 is coupled to or may be formed continuously with the retractable wedge 118. In this embodiment, the control rod 128 is coupled to a reverse gear 38 by a link 130. The reverse gear 38 is moveable by a corresponding lever gear 40 which is part of the actuator handle 22. A spring 42 coupled between a fixed spring anchor 44 and the actuator handle 22 such that the handle 22 is biased away from a grip 46 formed by the housing 24. With the handle 22 in the position shown in FIG. 6, the retractable wedge 118 is not retracted, but is, instead, in a piercing position.

Figure 7:
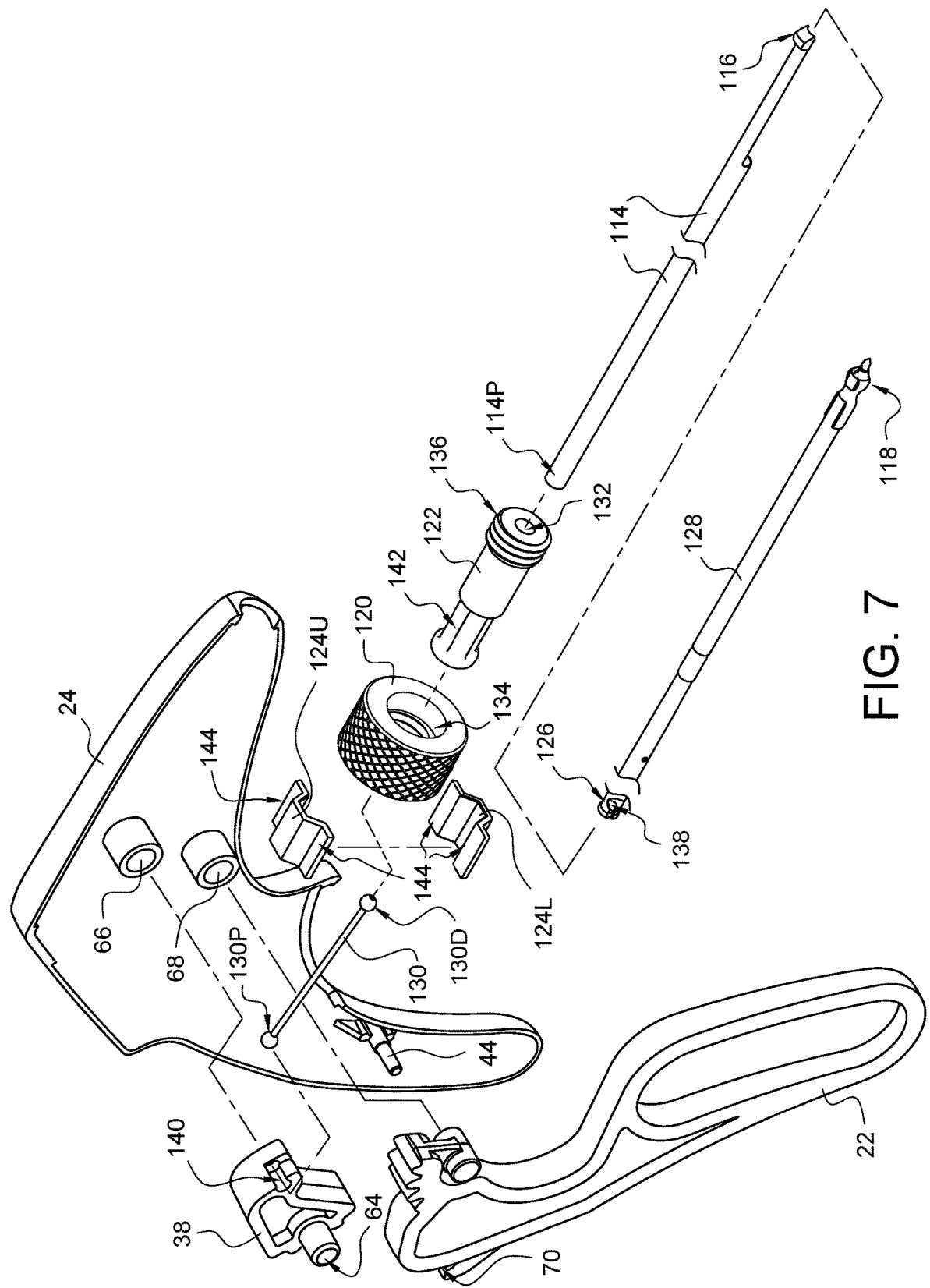
FIG. 7 is an exploded perspective view of the cannulation device of FIG. 6.

FIG. 7 is an exploded perspective view of the cannulation device 112 of FIG. 6. The proximal end 114P of the tube 114 is coupled inside a tube receiver 132 in the adapter 122. Threads 134 inside the adjustment nut 120 correspond to adapter threads 136 on the adapter 122, and the adjustment nut 120 may be threaded onto the adapter 122. In this embodiment, the retractable wedge 118 is formed continuously with the control rod 128 as part of the same part. In other embodiments, these portions could be separate parts and would need to be coupled. The proximal end 126 of the control rod 128 is placed into the tube 114 and extended through the adapter 122 until a distal end 130D of the link 130 can be coupled to the link end receiver 138 on the control rod 128. The control rod 128 can then be moved within the tube 114 so that the wedge tip 118 is aligned in a piercing position with the fixed blade 116 while the proximal end 130P of the link 130 is coupled to a link receiver 140 on the reverse gear 38. Reverse gear axles 64 are mated with corresponding reverse gear axle bosses 66 on the housing 24. Given the exposed perspective of FIG. 7, it should be noted that the visible reverse gear axle 64 mates with a boss in the housing that has been removed to expose the working parts (and therefore is not visible). Similarly, the visible reverse gear axle boss 66 mates with a gear axle 64 which is not visible from this perspective.

With the retractable wedge 118 fully extended in a piercing position, the actuator handle 22 can be pivotably coupled to the housing 24 while the handle 22 is fully extended. In doing this, axles 48 of the handle 22 are placed within corresponding lever axle bosses 68 of the housing 24. As with previous embodiments, the spring (not shown in this view) is coupled between a spring attachment point 70 on the handle 22 and a fixed spring anchor 44 on the housing 24.

The adapter 122 has facets 142 which are held by the upper and lower clamshell pieces 124U, 124L. The clamshell pieces 124U, 124L have housing interface tabs 144 which mate with corresponding features (not shown, but known to those skilled in the art) on the inside of the housing 24. Although only one half of the housing 24 is shown in this exposed exploded view, it should be understood that a corresponding half of the housing (not shown) would couple with the visible housing 24 half to hold the adapter 122 in place while providing for pivotable movement of the actuator handle 22 and reverse gear 38 so that the retractable wedge 118 may be moved as discussed with previous embodiments.

Various advantages of a cannulation device have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A cannulation device, comprising:
    a fixed blade comprising a key;
    a retractable wedge;
    an adjustment nut for mating with a cannula or a cannula assembly.

2. The cannulation device of claim 1, further comprising a tube having a key receiver.

3. The cannulation device of claim 2, wherein:
    the fixed blade is coupled to the tube; and
    the retractable wedge is slidable within the tube.

4. The cannulation device of claim 2, wherein the adjustment nut is movable to change a distance between the adjustment nut and the fixed blade.

5. The cannulation device of claim 2, wherein
    the key receiver is configured to mate with the key to prevent movement of the fixed blade in a direction substantially parallel to a longitudinal axis of the tube.

6. The cannulation device of claim 2, wherein the tube comprises the fixed blade.

7. The cannulation device of claim 1, further comprising an actuator coupled to the retractable wedge such that movement of the actuator between first and second positions causes the retractable wedge to move between a piercing position and a retracted position.

8. The cannulation device of claim 7, wherein the piercing position is a default position when no force is applied to the actuator.

9. The cannulation device of claim 1, wherein the fixed blade comprises a transition edge configured to cover a lead edge of a cannula.

10. The cannulation device of claim 1, further comprising a cannula adapter.

11. The cannulation device of claim 10, wherein the cannula adapter comprises:
    a strain relief;
    a hub body; and
    a sealing cap.

12. The cannulation device of claim 11, wherein the hub body comprises a fluid port.

13. The cannulation device of claim 11, wherein the sealing cap comprises a receiver configured to receive the fixed blade and the retractable wedge.

14. The cannulation device of claim 11, further comprising a cannula.

15. A cannulation device, comprising:
    a tube having a proximal end and a distal end;
    a fixed blade coupled to the distal end of the tube and wherein the fixed blade comprises a transition edge configured to cover a lead edge of a cannula;
    a control rod movable within the tube;
    a retractable wedge coupled to the control rod;
    an actuator coupled to the control rod and configured to move the retractable wedge from a piercing position where the retractable wedge is aligned with the fixed blade to a retracted position where the retractable wedge has been retracted within the tube;
    an adjustment nut movable to change a distance between the adjustment nut and the fixed blade; and
    a cannula adapter.

16. The cannulation device of claim 15, further comprising:
   a strain relief;
   a hub body; and
   a sealing cap.

* * * * *